US010031126B2

(12) United States Patent
Blake et al.

(10) Patent No.: US 10,031,126 B2
(45) Date of Patent: Jul. 24, 2018

(54) SYSTEM AND METHOD FOR UTILIZING EXHALED BREATH FOR MONITORING INFLAMMATORY STATES

(71) Applicant: THE REGENTS OF THE UNIVERSITY OF CALIFORNIA, Oakland, CA (US)

(72) Inventors: Donald R. Blake, Irvine, CA (US); Alan G. Barbour, Newport Beach, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 199 days.

(21) Appl. No.: 14/781,430

(22) PCT Filed: Apr. 4, 2014

(86) PCT No.: PCT/US2014/032928
§ 371 (c)(1),
(2) Date: Sep. 30, 2015

(87) PCT Pub. No.: WO2014/165732
PCT Pub. Date: Oct. 9, 2014

(65) Prior Publication Data
US 2016/0033476 A1    Feb. 4, 2016

Related U.S. Application Data

(60) Provisional application No. 61/808,540, filed on Apr. 4, 2013.

(51) Int. Cl.
*G01N 33/49*      (2006.01)
*G01N 33/497*     (2006.01)

(52) U.S. Cl.
CPC ... *G01N 33/497* (2013.01); *G01N 2033/4975* (2013.01)

(58) Field of Classification Search
CPC ................... G01N 33/497; G01N 2033/4975
See application file for complete search history.

(56) References Cited

U.S. PATENT DOCUMENTS 5,293,875 A    3/1994 Stone
6,764,831 B2   7/2004 Cameron, Sr. et al.
(Continued)

FOREIGN PATENT DOCUMENTS

WO    WO 03/094932    11/2003

OTHER PUBLICATIONS

Cheepsattayakorn, Attapon et al., "Breath Test in Respiratory and Critical Care Medicine: From Research to Practice in Current Perspectives", BioMed Research International, 2013.*
(Continued)

*Primary Examiner* — Paul West
(74) *Attorney, Agent, or Firm* — Vista IP Law Group LLP

(57) ABSTRACT

A system for monitoring an exhaled breath of a subject is described. A breath collector can be configured to receive exhaled breath from a subject. One or more sensors can be configured to output a concentration of a first gas compound in the received exhaled breath, and to output a concentration of a second gas compound in the received exhaled breath. The second gas compound is used to normalize the concentration of the first gas based on different physiological states of the subject. A processor operably coupled to the one or more sensors is configured to calculate a ratio of the first gas compound to the second gas compound based on the determined concentrations, and to determine a normalized concentration of the first gas compound. This ratio may be monitored to evaluate an inflammatory state of the subject.

15 Claims, 12 Drawing Sheets

(56) References Cited

U.S. PATENT DOCUMENTS

| | | |
|---|---|---|
| 7,153,272 B2 | 12/2006 | Talton |
| 7,306,953 B2 | 12/2007 | Probert et al. |
| 7,547,285 B2 | 6/2009 | Kline |
| 7,678,390 B2 | 3/2010 | Choi et al. |
| 8,348,853 B2 | 1/2013 | Altobelli et al. |
| 2008/0220984 A1 | 9/2008 | Bright et al. |
| 2008/0275355 A1* | 11/2008 | Namjou-Khaless . A61B 5/0059 600/532 |

OTHER PUBLICATIONS

Ryter, Stefan W., "Carbon Monoxide in Exhaled Breath Testing and Therapeutics", Journal of Breath Research, Feb. 27, 2013.*

Gajdocsy, Reka et al., Exhaled carbon monoxide in airway diseases: from research findings to clinical relevance, J. Breath Res. 4 (2010) 047102 (7pp).

Morimatsu, Hiroshi et al., An increase in exhaled CO concentration in systemic inflammation/sepsis, J. Breath Res. 4 (2010) 047103 (4pp).

Ryter, Stefan W. et al., Carbon Monoxide in Exhaled Breath Testing and Therapeutics, J Breath Res. Author manuscript; available in PMC Mar. 1, 2014; J. Breath Res. Mar. 2013; 7(1):017111. doi:10.1088/1752-7155/71/017111.

PCT International Search Report for PCT/U52014/032928, Applicant: the Regents of the University of California, Form PCT/ISA/210 and 220, dated Sep. 4, 2014 (4pp).

PCT Written Opinion of the International Search Authority for PCT/US2014/032928, Applicant: The Regents of the University of California, Form PCT/ISA/237, dated Sep. 4, 2014 (7pp).

PCT International Preliminary Report on Patentability (Chapter I of the Patent Cooperation Treaty) for PCT/US2014/032928, Applicant: The Regents of the University of California, Form PCT/IB/326 and 373, dated Oct. 15, 2015 (9pages).

Barbour, Alan G. et al., Isolation and Cultivation of Lyme Disease Spirochetes, The Yale Journal of Biology and Medicine, 57, (1984), 521-525.

Barbour, Alan G. et al., Niche Partitioning of Borrelia burgdorferi and Borrelia miyamotoi in the Same Tick Vector and Mammalian Reservoir Species, Am. J. Trop. Med. Hyg., 81 (6), 2009, pp. 1120-1131.

Barbour, Alan G., Relapsing Fever, Department of Medicine and Microbiology & Molecular Genetics, University of California Irvine, Irvine, CA, 2004 (60 pages).

Buszewski, Bogustaw et al., Human exhaled air analytics: biomakers of disease, Biomed. Chromatogr. 21: 553-566 (2007).

Chung, Su Wol et al., Heme oxygenase-1-derived carbon monoxide enhances the host defense response to microbial sepsis in mice, J. Clin. Invest. 118:239-247 (2008). doi:10.1172/JCI32730.

Dai, Qiyuan et al., Antigenic variation by Borrelia hermsil occurs through recombination between extragenic repetitive elements on linear plasmids, Molecular Microbiology (2006). doi:10.1111/j.1365-2958.2006.05177.x.

Epiphanio, Sabrina et al., Heme Oxygenase-1 Is an Anti-Inflammatory Host Factor that Promotes Murine Plasmodium Liver Infection, Cell Host & Microbe 3, 331-338, May 2008.

Fraser, Claire et al., Genomic sequence of a Lyme disease spirochaete, Borrelia burgdorferi, Nature, vol. 390, Dec. 11, 1997.

Guaman, Ana V. et al., Rapid detection of sepsis in rats through volatile organic compounds in breath, Journal of chromatography B, 881-882 (2012) 76-82.

Kamboures, M.A. et al., Breath sulfides and pulmonary function in cystic fibrosis, Proc Natl Acad Sci USA. Nov. 1, 2005; 102(44): 15762-15767.

Kazragis, Robert J. et al., In Vivo Activities of Ceftriaxone and Vancomycin against Borrelia spp. in the Mouse Brain and Other Sites, Antimicrobial Agents and Chemotherapy, Nov. 1996, p. 2632-2636.

Kitten, Todd et al., The Relapsing Fever Agent Borrelia hermsii Has Multiple Copies of Its Chromosome and Linear Plasmids, Genetics 132:311-324 (Oct. 1992).

Lescot, Magali et al., The Genome of Borrelia recurrentis, the Agent of Deadly Louse-Borne Relapsing Fever, Is a Degraded Subset of Tick-Borne Borrelia duttonii, PLoS Genetics, www.plosgenetics.org., Sep. 2008, vol. 4, Issue 9, e1000185.

Ligor, Magdalena et al., Determination of volatile organic compounds in exhaled breath of patients with lung cancer using solid phase microextraction and gas chromatography mass spectrometry, Clin Chem Lab Med 2009;47 (5):550-560, 2009 by Walter de Gruyter. Berlin. New York. DOI 10.1515/CCLM.2009.133.

Meinardi, Simone et al., Exhaled breath and fecal volatile organic biomarkers of chronic kidney disease, Biochimica et Biophysica Acta 1830 (2013) 2531-2537.

Morimatsu, Hiroshi et al., Increased heme catabolism in critically ill patients: correlation among exhaled carbon monoxide, arterial carboxyhemoglobin, and serum bilirubin IXa concentrations, Am J Physiol Lung Cell Mol Physiol 290:L114-L119, 2006.

Motterlini, Roberto et al., The therapeutic potential of carbon monoxide, Nature Reviews, Drug Discovery, vol. 3, Sep. 2010, 728-742, www.nature.com/reviews/drugdisc.

Novak, B.J. et al., Exhaled methyl nitrate as a noninvasive marker of hyperglycemia in type 1 diabetes, PNAS, Oct. 2, 2007, vol. 104, No. 40, 15613-15618.

Rochette, Luc et al., Carbon monoxide: Mechanisms of action and potential clinical implications, Pharmacology & Therapeutics 137 (2013) 133-152.

Ryter, Stefan W. et al., Heme Oxygenase-1/Carbon Monoxide: From Basic Science to Therapeutic Applications, Physhiol Rev 86: 583-650, 2006; doi:10.1152/physrev.00011.2005.

Simpson, I.J. et al., Characterization of trace gases measured over Alberta oil sands mining operations: 76 speciated C2-C10 volatile organic compounds (VOCs), CO2, CH4, CO, NO, NO2, NOy, O3 and SO2, Atmos. Chem. Phys., 10, 11931-11954, 2010, www.atmos-chem-phys.net/10/11931/2010/, doi:10.5194/acp-10-11931-2010.

Schulz, Stephanie et al., Metalloporphyrins—an update, Frontiers in Pharmacology, Drug Metabolism and Transport, Apr. 2012, vol. 3, Article 68, 1-16, www.frontiersin.org.

Vautz, Wolfgang et al., Analyses of mouse breath with ion mobility spectrometry: a feasibility study, J Appl Physiol 108:697-704, 2010.

Walther, Michael et al., HMOX1 Gene Promoter Alleles and High HO-1 Levels Are Associated with Severe Malaria in Gambian Children, PLoS Pathogens, www.plospathogens.org, Mar. 2012, vol. 8, Issue 3, e1002579.

Wegial, Barbara et al., The social network of carbon monoxide in medicine, Trends in Molecular Medicine, Jan. 2013, vol. 19, No. 1.

Yachie, Akihiro et al., Heme Oxygenase-1 Production by Peripheral Blood Monocytes During Acute Inflammatory Illnesses of Children, Monocyte HO-1 in Inflamatory Diseases, 550-556, copyright 2003 by the Society for Experimental Biology and Medicine.

Zegdi, Rachid et al., Increased endogenous carbon monoxide production in severe sepsis, Intensive Care Med (2002) 28:793-796.

Zhong, Jianmin et al., Cross-species hybridization of a Borrelia burgdorferi DNA array reveals infection- and culture-associated genes of the unsequenced genome of the relapsing fever agent Borrelia hermsii, Molecular Microbiology (2004) 51(3), 729-748.

\* cited by examiner

| Normalized CO concentration | Disease state for sepsis |
|---|---|
| <500 | No infection |
| Equal to or > 500 | Infection |

FIG. 3

SYSTEM AND METHOD FOR UTILIZING EXHALED BREATH FOR MONITORING INFLAMMATORY STATES

RELATED APPLICATIONS

This Application is a U.S. National Stage filing under 35 U.S.C. § 371 of PCT Patent Application No. PCT/US2014/032928, filed Apr. 4, 2014, which claims priority to U.S. Provisional Patent Application No. 61/808,540 filed on Apr. 4, 2013. The contents of the aforementioned applications are incorporated by reference herein. Priority is expressly claimed in accordance with 35 U.S.C. § § 119, 120, 365 and 371 and any other applicable statutes.

STATEMENT REGARDING FEDERALLY SPONSORED RESEARCH AND DEVELOPMENT

This invention was made with Government support under Grant No. AI065359 awarded by the National Institutes of Health. The Government has certain rights in this invention.

FIELD OF THE INVENTION

The field of the invention generally relates to breath analysis devices and methods. More particularly, the field of the invention relates to a method and a system of diagnosing and/or monitoring a disease state based on concentrations of one or more gases in the exhaled breath of a subject.

BACKGROUND

Blood analysis is typically a preferred choice in most laboratory tests for diagnosis and disease monitoring. However, assays of blood are seldom performed at the bedside, and it may be hours or days before results are known. When a subject's status is rapidly changing, and supportive and therapeutic maneuvers are underway, such as in an intensive care unit, real-time data on the function of the cardiovascular, respiratory, and other systems is of critical importance for distinguishing salutary from counterproductive actions. Non-invasive techniques involving body temperature, respiratory rate, and pulse rhythm have been historically known to be informative parameters for diagnosing, staging, and monitoring disease. Ancient physicians also recognized the diagnostic utility of smelling the exhaled breath for tell-tale aromas, such as with hepatic or renal failure. For some conditions, including, but not limited to, bacterial infections, malaria, diabetes, cystic fibrosis and cancer, analysis of exhaled breath may be a sufficiently accurate test that may help in clinical decision making. Thus, a means to analyze exhaled breath of a subject (and identify certain gaseous compounds in them) with sufficient sensitivity and discrimination may be hugely beneficial in diagnosis and treatment of certain disease states. In view of the above, a cost-effective, compact and accurate automated breath analyzer that can be used at the point-of-care is highly desirable.

SUMMARY

In one embodiment, a method of monitoring a subject's inflammatory state over time is disclosed. The method comprises collecting a set of samples of exhaled breath from a subject over a period of time, determining a normalized concentration of a first gas compound in each collected sample of exhaled breath, determining a change in the normalized concentration of the first gas compound over the period of time, and evaluating an inflammatory physiological state of the subject based on the determined change in the normalized concentration of the first gas compound. The normalized concentration of the first gas compound may be determined as a function (e.g., a ratio) of a concentration of a second gas compound in the sample of exhaled breath. In some embodiments, the first gas compound is CO while the second gas compound is $CO_2$. The inflammatory state may be caused or otherwise affected by, an infection (e.g., viral, bacterial, parasitic, fungal), a disease such as an autoimmune disease, or trauma (e.g., caused by surgery). The normalized concentration of the first gas compound can provide a proxy or correlation to the inflammatory state of the subject (e.g., human or animal).

In one embodiment, a method of diagnosing a disease state is disclosed. The method comprises collecting a sample of exhaled breath from a subject, determining a concentration of a first gas compound (e.g., carbon monoxide) in the collected sample, determining a concentration of a second gas compound (e.g., carbon dioxide) in the collected sample, calculating a ratio of the concentration of the first gas compound to the concentration of the second gas compound to determine a normalized concentration of the first gas compound, and diagnosing a disease state based on the determined concentration of the first gas. The method may further comprise comparing the determined concentration of the first gas compound to a predetermined set of values of concentration levels for the first gas compound, each concentration level representative of a stage of the disease state, and when the determined concentration exceeds a particular predetermined value, diagnosing the subject with a corresponding stage of the disease state.

The method may further comprise administering a treatment regimen to the subject based on the corresponding stage of the disease state, determining a follow-up concentration of the first gas compound in another collected sample of exhaled breath from the subject, the other sample collected after the appropriate treatment regimen has commenced, and evaluating an effectiveness of the appropriate treatment regimen based on the determined follow-up concentration of the first gas compound.

In another embodiment, a device for collecting exhaled breath from a subject is disclosed. The device comprises a breath collector configured to receive exhaled breath from a subject, one or more sensors configured to output a concentration of a first gas compound in the received exhaled breath, and to output a concentration of a second gas compound in the received exhaled breath, and a processor operably coupled to the one or more sensors and further configured to calculate a ratio of the concentration of the first gas compound to the concentration of the second gas compound to determine a normalized concentration of the first gas compound. In some alternative configurations, the processor may be further configured to output a diagnosis of a disease state based on the normalized concentration of the first gas compound (e.g., infection vs. non-infection). The processor may be configured to output a time-stamped, normalized concentration of the first gas compound such that time-based study or observation can be made over a period of time. The sensor may be a laser gas trace monitor. The sensor may output real-time or near real-time concentrations of the first gas compound and the second gas compound.

In some embodiments, the processor may compare the normalized concentration of the first gas compound to a set of predetermined values representative of the presence or absence of a disease state, wherein the presence or absence of the disease state is output when the normalized concentration of the first gas compound exceeds a corresponding predetermined value.

BRIEF DESCRIPTION OF THE DRAWINGS

FIG. 3 is a table illustrating a list of CO concentrations measured by the breath analysis device of the type illustrated in FIG. 1 and associated disease states.

DETAILED DESCRIPTION OF THE ILLUSTRATED EMBODIMENTS

Figure 1:
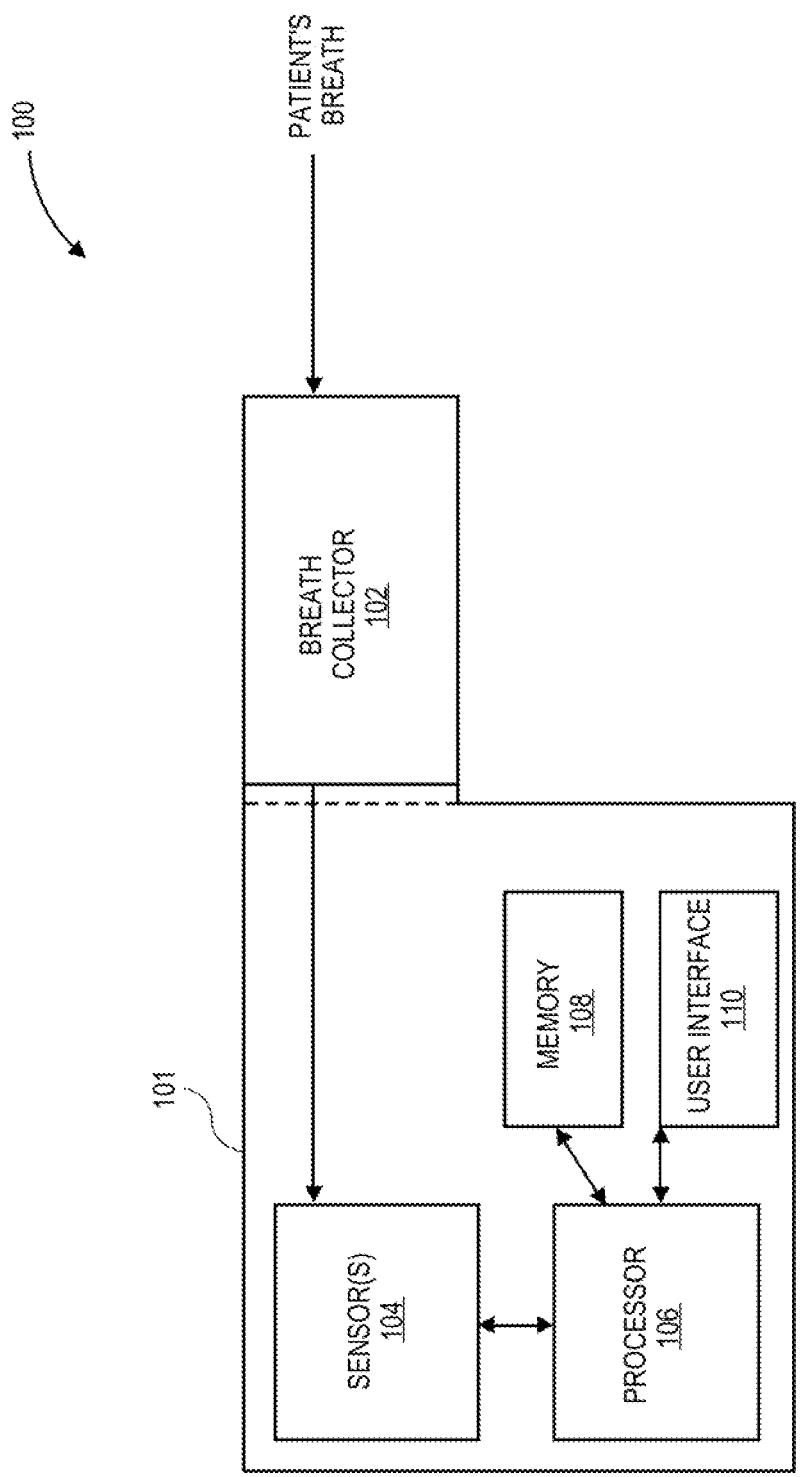
FIG. 1 illustrates a block diagram of the system of a breath analysis device according to one embodiment.

FIG. 1 illustrates a system 100 for analyzing the exhaled breath of a subject. The analysis performed by the system 100 may include measuring the concentration of one or more constituents of the exhaled breath. In one embodiment as described herein, the concentration of one breath constituent may be normalized against the concentration of another breath constituent. The system 100 may be used to diagnose, monitor, and/or evaluate the subject based on the analysis performed using a breath analysis device 101. In one particular embodiment, the breath analysis device 101 generally includes a breath collector 102, a plurality of sensors 104 disposed in or otherwise associated with the breath collector 102, one or more processors 106, and an optional user display 108. The breath analysis device 101 may be used for bed-side monitoring of the subject, and to render results based on the exhaled breath of the subject. In some embodiments, bed-side monitoring may also be used for diagnostic purposes. In particular, the breath analysis device 101 may include a breath collector 102 for collecting a sample of exhaled breath from a subject. In an optional embodiment, the breath analysis device may also collect a sample of inhaled breath from the subject. The breath collector 102 collects, at least temporarily, exhaled or expelled air (and inspired air, in some embodiments) from the subject. For example, in some embodiments, gas passing by a sensor that is not physically retained in any vessel or container is still referred to as being collected. An example of this may be a mask that is worn by a subject through which passes exhaled air (and inspired air).

In embodiments that include collecting inhaled air or air that will be inhaled, the sample of inhaled breath may simply be a sample of ambient air in the environment that is representative of air inhaled by the subject. In another embodiment, the subject may breathe through a breathing tube, a sample of which may be collected in the breath collector 102. In yet another embodiment, if the subject is in a special environment (e.g., an incubator in the case of neonatal subjects), the sample may be taken from the ambient air of the special environment that is representative of the air being inhaled by the subject. Measurements may be taken in situ or perhaps in a gas blender or mixer that provides a mixed source of gas to a subject.

In some embodiments, the exhaled breath of the subject may be more permanently collected through a bag, container or other collection apparatus coupled to the breath collector 102. The subject may breathe into the breath collector 102 that is associated with the bag, container, or other collection apparatus.

In one embodiment, if inhaled air is being collected, both inhaled and exhaled breath may be sampled through the same breath collector 102. For example, the breath collector 102 may first sample the inhaled breath (e.g., ambient air, air inside an incubator, etc.), analyze the inhaled breath for gas concentrations of one or more gaseous constituents, and then sample and analyze the exhaled breath of the subject. In an alternate embodiment, there may be multiple breath collectors: one for inhaled breath, and another for exhaled breath. Of course, in other embodiments, only the exhaled or expired air is sampled through the breath collector 102.

The breath collector 102 contains therein one or more sensors 104. The sensor(s) 104 are configured for sensing one or more gaseous compounds in the collected breath sample, and measuring real-time or near real-time concentrations of the gaseous compounds in the collected breath sample. Each of the sensors 104 may be configured for sensing a particular gaseous compound, or there could be a sensor 104 that may be able to sense a plurality of gaseous compounds. In one illustrative embodiment, the sensor 104 may be a sensor that uses coherent or laser light to measure gas concentrations. An example of such a laser-based gas monitors include laser-trace monitors (e.g., dual channel, quantum cascade laser trace gas monitor available from Aerodyne Research, Inc. (Billerica, Mass.)).

Although any gaseous sample may be selected for sensing purposes, it has been observed in various animal experiments (experimental results discussed in detail below) that elevated levels of carbon monoxide (CO) correlate to inflammatory physiological states. The inflammation may be caused by an infection (e.g., bacterial infections, viral infections, fungal infections, infections due to parasites, etc.) or may be a due to a severe autoimmune disease, a major surgery or any other major trauma. Regardless of the cause of the inflammation, however, CO levels can be used to monitor an inflammatory state or status. Thus, CO may be used as a parameter or proxy of inflammatory physiological states, and monitoring CO levels in the subject may help the user evaluate a subject's condition, monitor the subject's condition over a period of time, and in some instances, may even diagnose the subject. Thus, although the breath analysis device 101 may be configured to measure concentrations of any gaseous compound, the following discussion will focus on measuring CO for illustrative purposes. Other gaseous compounds expired by subjects include, for example, nitric oxide, ethyne or the like.

In one embodiment that measures the concentration of CO, the sensor(s) 104 are configured for measuring real-time or near real-time concentrations of at least two gaseous compounds. In a preferred embodiment, the sensors 104 also measure concentration of at least a second gaseous compound that used as a control. For example, the measured concentration may vary depending on subject's individual breathing pattern. It should be appreciated that the concentration of the second gaseous compound is then used to normalize the measured concentration of the first gaseous compound, as will be described in further detail above. Similar to above, although any gaseous compound that is routinely found in exhaled breath may be used, carbon dioxide ($CO_2$) may effectively be used for normalization purposes. Thus, for illustrative purposes, the following discussion will focus on measuring $CO_2$ for normalization purposes.

The sensor(s) 104 are operatively coupled to a processor 106 (e.g., a central processing unit (CPU)) configured for analyzing the concentrations of the gaseous compounds sensed and measured by the sensor(s) 104. The processor 106 receives the measured concentration data (or signals representative of concentration data) from the sensor(s) 104, and, for each of the sensed gaseous compound, uses the concentration data to monitor the inflammatory state of the subject. Alternatively, or in addition to, the processor 106 may diagnose a disease state the subject. It should be appreciated that the processor 106 may use the concentration data for other types of data analysis as well. Power is supplied via a source of AC or DC power (not shown).

In one embodiment, if inhaled breath was also collected through the breath analysis device 101, the processor 106 may optionally subtract, for each of the sensed gases, the concentration of that gas in the inhaled breath from that in the exhaled breath of the subject to determine the difference. It should be appreciated that computing this difference in concentrations of both gaseous compounds may be important in order to only account for gaseous compounds that are released by the subject. In other words, simply using the concentration of a gaseous compound in the exhaled breath of a subject may lead to erroneous results because the subject may simply have inhaled a large concentration of that particular gaseous compound (e.g., the subject may be breathing air having high concentrations of CO). Thus, computing the difference between exhaled and inhaled breath ensures that only CO released as a result of metabolic processes in the subject is accounted for. Of course, in other embodiments, the subtraction operation may be omitted and only the concentration of CO in the expired air may be measured.

The processor 106 is configured for using the difference value of each of the gaseous compounds to normalize the concentration of the first gaseous compound in relation to the second gaseous compound that is indicative of the subject's breathing pattern. To this end, the processor 106 calculates a ratio of the concentration of the first gaseous compound to the second gaseous compound to generate a normalized concentration of the first gaseous compound.

In one embodiment, based on the normalized concentration of the first gaseous compound, the processor 106 is further configured for determining a disease state of the subject based on the normalized concentration of first gaseous compound in the exhaled breath of the subject. For example, the normalized concentration that is calculated could be compared to a look up table, calibration curve, or the like stored in a memory 108. In this example, if the normalized concentration exceeds a curtained pre-determined threshold, the processor 106 may output a signal to user interface 110 that indicates that a subject has a particular disease state. As mentioned above, the disease state may be an infection (viral, bacterial, fungal, or parasitic infection) or other disease state. CO has been observed to be high in cases with certain bacterial infections.

As noted above, the breath analysis device 101 may further comprise a memory 108 that may store software for performing the calculations discussed herein (e.g., subtractions and ratios). The memory 108 may also store look-up-tables or other calibration curves used to discern a disease state based on the measured concentrations of gaseous compound(s) exhaled by the subject. The processor 106 may be configured for selecting the disease state by matching the normalized concentration of the first gaseous compound with one of the disease states of the look-up-table or other calibration curve. It should be appreciated that in optional embodiments, the breath analysis device 101 may simply output the normalized concentration of CO in the exhaled breath, which may be further analyzed to manually diagnose the subject.

The breath analysis device 101 may further comprise a user interface 110 that allows a user (e.g., a doctor, a clinician, etc.) to interact with the breath analysis device 101. The user interface 110 may comprise a user input module (e.g., a mouse, a keyboard, etc.) to provide user commands to the breath analysis device 101. For example, the user may manually enter information related to subject symptoms etc., in one embodiment. The user interface 110 may further comprise a user display (e.g., a monitor, a smartphone display, etc.) enabling the user to view a set of information outputted by the breath analysis device 101. This could be, for example, the $CO/CO_2$ ratio.

In an optional embodiment, the breath analysis device 101 may be configured to communicate with a network such as a LAN or WAN (not shown), such that the results from the breath analysis device is automatically uploaded to the cloud and accessed by other computes of the network. Such connections may be wired or wireless.

The breath analysis device 101 may further include a power source (not shown). The power source may include one or more batteries. For example, the batteries may include two AA batteries. Or, in another example, the power source maybe connected to a traditional AC power outlet.

It should be appreciated that the components of breath analysis device 101 may be housed in a single case, or may be housed separately. For example, if housed separately, the breath collector 102 (coupled to the sensor(s) 104) may be a detachable component that collects exhaled breath (and optionally inhaled breath) at the subject's bed-side and communicates with the processor 106. Or, the components of the breath analysis device may be housed in a single compact device containing the above mentioned components.

Figure 2:
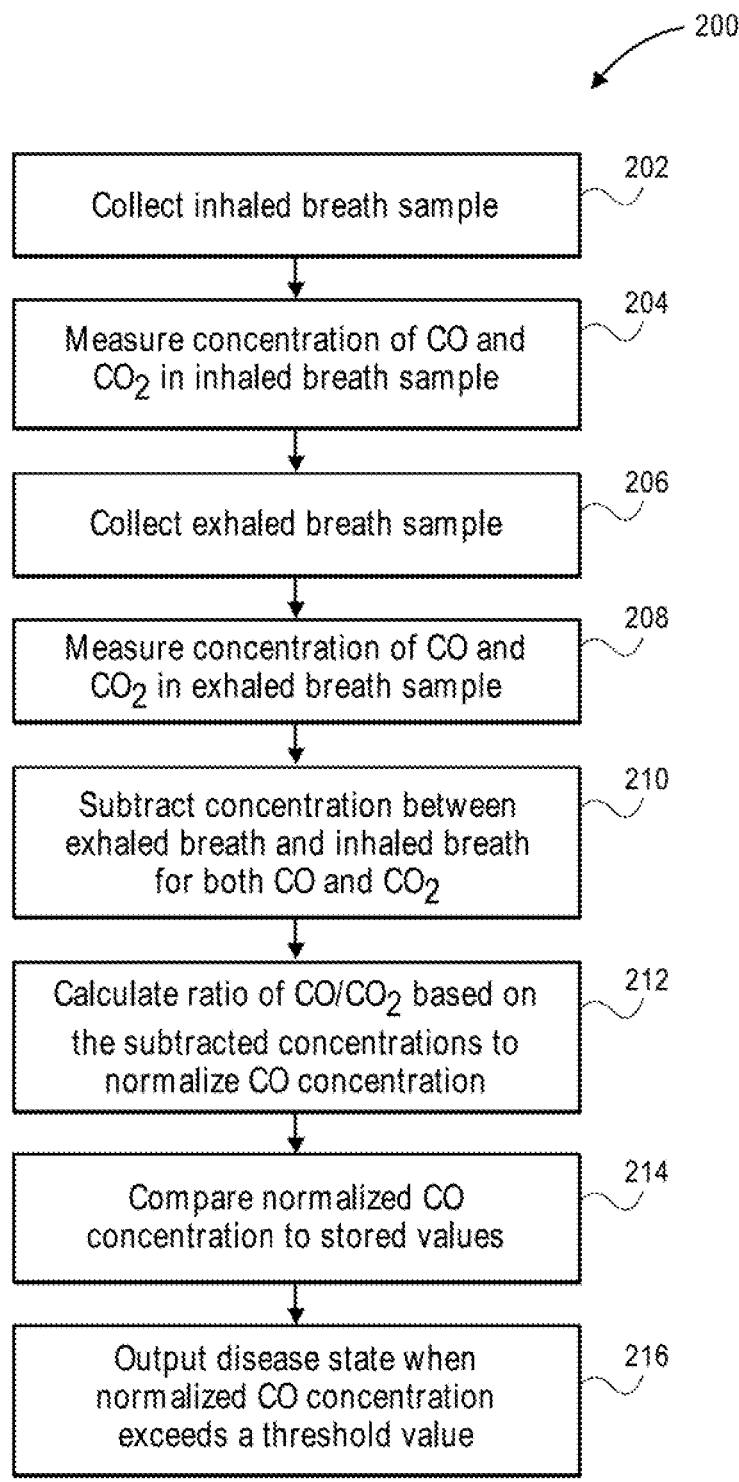
FIG. 2 illustrates a method of using the breath analysis device of FIG. 1 according to one embodiment.

Referring now to FIG. 2, an exemplary method 200 for diagnosing a disease state based on the analyzed breath using the breath analysis device 101 will be described. For illustrative purposes, the following discussion will focus on a breath analysis device that measures the concentration of CO and $CO_2$ in both inhaled and exhaled breath of the subject, and diagnoses the subject based on the concentration of CO in the exhaled breath of the subject.

First, the breath analysis device 101 collects a sample of inhaled breath from the subject (step 202). As mentioned previously, the inhaled breath may simply be a sample of the ambient air surrounding the subject. This is used to determine the background levels of CO and $CO_2$ which are then subtracted out to give a reading of the net CO and $CO_2$ produced by the subject in some embodiments. The breath analysis device 101 measures concentrations of both CO and $CO_2$ in the inhaled breath of the subject (step 204).

Next, the breath analysis device 101 collects a sample of exhaled breath from the subject (step 206). For example, the subject may breathe into the breath collector of the breath analysis device 101 for a predetermined amount of time, in one embodiment. Again, the breath analysis device 101 measures concentrations of both CO and $CO_2$ in the exhaled breath of the subject (step 208). As mentioned above, it should be appreciated that in some embodiments, the inhaled and exhaled breath may be sampled over one or more breathe cycles.

Next, the breath analysis device 101 subtracts the concentration of CO in the inhaled breath (or other background source) from the concentration of CO in the exhaled breath to determine the concentration of CO exhaled by the subject. Similarly, the breath analysis device 101 subtracts the concentration of $CO_2$ in the inhaled breath (or other background source) from the concentration of $CO_2$ in the exhaled breath to determine the concentration of $CO_2$ exhaled by the subject (step 210). As mentioned previously, this is an important step that accounts for the concentration of a particular gas in the surrounding air to ensure that the diagnosis of the disease state is based on the net contribution of CO and $CO_2$ released from the subject. It should be understood, however, that in some embodiments, the subtraction step may be omitted entirely in that there is no need to subtract the inhaled or other background concentrations of CO and $CO_2$.

Next, the breath analysis device 101 calculates a ratio of the exhaled CO and exhaled $CO_2$ to normalize the concentration of CO (step 212). Normalization accounts for a particular subject's breathing pattern and capacity. For example, a first subject may have trouble breathing and may output only a small amount of air (i.e., low level of CO), while a second subject may have a large lung capacity and routinely output a large amount of air (i.e., a higher level of CO) during the same time period. Thus, comparing just the concentration of CO across subjects may lead to erroneous results for the purposes of diagnosis. To this end, determining the exhaled CO concentration as a function of the exhaled $CO_2$ concentration ensures a more accurate reading (i.e., the first subject may have a low concentration of CO and $CO_2$, and the second subject may have a high concentration of CO and $CO_2$). Thus, assuming both the first and the second subjects are healthy, the normalized CO concentrations for both subjects are now on an equal footing, leading to more accurate diagnosis.

Next, the breath analysis device 101 compares the normalized CO concentration to a stored value (step 214). As mentioned previously, a look-up-table or graph contains a list or function of CO concentrations and establishes a threshold concentration above which is indicative of a disease state. The breath analysis device 101 may diagnose the subject comparing the normalized concentration that was measured by the breath analysis device 101 with a threshold value stored in the memory 108 and outputting a signal or other indicia of a disease state when this number is exceeded (step 216).

In another exemplary embodiment, the breath analysis device 101 may measure the concentration of CO and $CO_2$ in only the exhaled breath of the subject. In this regard, there is no subtraction step needed and may be omitted. The subject may be monitored using the ratio of CO and CO2 as explained herein. In other embodiments, the subject may be diagnosed based on the concentration of CO in the exhaled breath of the subject.

First, the breath analysis device 101 collects a sample of exhaled breath from the subject and measures concentrations of both CO and $CO_2$ in the exhaled breath of the subject. Next, the breath analysis device 101 calculates a ratio of the exhaled CO and exhaled $CO_2$ to normalize the concentration of CO. Additional samples of expired air may be obtained at various times and the ratio can be calculated. The time-wise progression of the ratio may be monitored over a period of time. The breath analysis device 101 may output this ratio periodically.

In some embodiments, the breath analysis device 101 compares the normalized CO concentration to a stored value. The stored value may represent a threshold value that represents a cutoff used for a diagnosis. In this embodiment, the breath analysis device 101 may diagnose the subject comparing the normalized concentration that was measured by the breath analysis device 101 with a threshold value stored in the memory 108 and outputting a signal or other indicia of a disease state when this number is exceeded.

Referring now to FIG. 3, one exemplary embodiment of selecting a disease state based on the normalized CO concentration is illustrated. If the normalized CO concentration is less than 500, the breath analysis device 101 selects a disease state of "no infection." If the normalized CO concentration is equal to or greater than 500, the breath analysis device 101 selects the disease state of "infection". In other embodiments, the look-up table may contain more disease states. For example, instead of having just two disease states—either a positive or a negative of a disease state—the breath analysis device 101 may contain levels of the disease state (e.g., not infected, mildly infected, highly infected, etc.) (not shown). Or, the look-up-table may have multiple disease states such that the breath analysis device 101 diagnoses one of a plurality of diseases depending on the gas or gas combination that is measured.

Rather than be used for strict diagnosis purposes, in some embodiments, the breath analysis device 101 may be used to monitor a subject to assess the subject for general health or possible inflammatory conditions or states. For example, a subject may enter a medical facility such as a hospital, care clinic, or medical office and be initially tested with the breath analysis device 101. Such tests may continue for a period of time, e.g., hours, days, or weeks whereby the normalized CO levels over a period of time are measured. In this embodiment, the absolute level of normalized CO level may not be as important as the change in the normalized CO level over time. The change in the normalized CO level over time may be used to evaluate a physiological state (e.g., a state of inflammation in the body, a state of oxidative stress in the body, etc.) of the subject. For example, an increase in the normalized CO level may be indicative that the subject's inflammatory condition is worsening over time. For example, if the subject has an infection, this may indicate a progression of infection within the subject.

Figure 4:
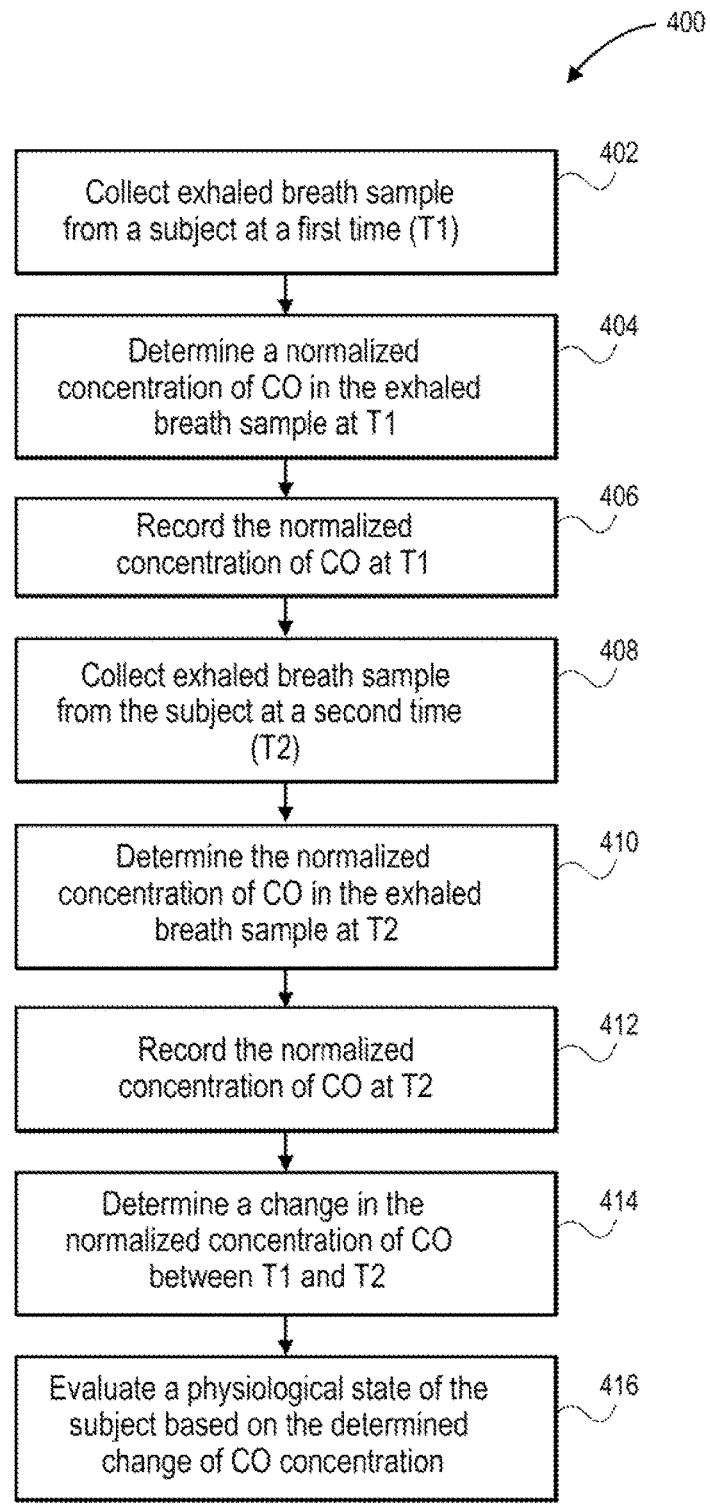
FIG. 4 illustrates a method of using the breath analysis device of FIG. 1 to monitor a physiological state of a subject according to one embodiment.

Referring now to FIG. 4, an exemplary method 400 of monitoring the physiological state of a subject using the breath analysis device 101 is described. For illustrative purposes, the following discussion will assume that both inhaled and exhaled breath is collected from the subject. As mentioned herein, however, the method may also just examine the exhaled breath of the subject.

First, the exhaled breath of a subject is collected at a first time (T1) (step 402). For example, the subject may breathe into the breath analysis device 101 when first admitted to a treatment facility. Next, the breath analysis device 101 determines a normalized concentration of CO in the exhaled breath of the subject at T1 (step 404).

Next, the breath analysis device 101 records the normalized concentration of CO for the subject at T1 (step 406). For example, the breath analysis device 101 may automatically time-stamp a CO concentration reading for each subject. Or, in an alternate embodiment, the breath analysis device 101 may be programmed to track, over a period of time, a set of normalized CO readings for the subject. Or, the user may manually (or through the same or a separate processor) record the normalized CO concentration for the subject over time.

Next, the exhaled breath of the subject is collected at a second time (T2) (step 408). For example, the subject may breathe into the breath analysis device 101 on a daily basis; thus T2 may refer to day 2 at the treatment facility. Next, as above, the normalized concentration of the subject is determined at T2 (step 410) and recorded (step 412).

Next, based on the determined CO concentrations of the subject at T1 and T2, the breath analysis device 101 may determine a change in the CO concentration between T1 and T2 (step 414). Next, based on the determined change in the CO concentration, the physiological state of the subject may be evaluated (step 416). For example, there may be an increase in normalized CO concentration between day 1 (T1) and day 2 (T2) for the subject. This may indicate an increase in inflammation or oxidative stress in the body, and the user may tailor a treatment regimen based on this information. Or, the normalized CO concentration may be relative stable between T1 and T2, indicating to the user that the subject's condition is somewhat stable. Thus, the breath analysis device 101 may serve as a non-invasive tool to monitor the subject's physiological state over a period of time. Although the foregoing sample describes a simplified two day scenario of monitoring the subject, it should be appreciated that breath samples may be taken every day and recorded, such that the user can evaluate the physiological condition of the subject over longer periods of time. Moreover, the breath samples may be taken more frequently, for example, after hours or minutes have elapsed in which case the subject's monitored physiological state is monitored more frequently.

It should be appreciated that the breath analysis device 101 may also be used to determine if a particular treatment regimen is working. Given that the breath analysis device 101 offers a non-invasive method of quickly collecting subject data from the subject, the user may be able to monitor the progress of a treatment regimen that is being given to a subject. For example, the user may user the breath analysis device 101 to determine that the subject has a particular bacterial infection and administer some antibiotics to the subject. The user may then again have the subject breathe into the breath analysis device 101 after a few hours. If the levels of normalized CO have declined, it may indicate to the user that the antibiotic regimen is working. If, however, the normalized CO levels are consistent with the prior reading, the user may rethink treatment strategy, and administer a different treatment program for the subject.

It should also be appreciated that the results of the breath analysis device 101 may be used to correlate concentrations of protein compounds in the blood of the subject, and the disease state may, in turn, be diagnosed based on the correlated concentration of the protein compounds. More specifically, as briefly discussed above, the increased levels of CO in the exhaled breath of the subject may be indicative of inflammation and/or oxidative stress on the subject. For example, in animal experiments (discussed further below), it was found that the source of endogenous CO was attributable to the action of the enzyme heme oxygenase-1. Or, the protein compound may be mRNA of a particular gene that is being expressed. Based on this information (and optional blood tests/assays), the user may be able to better tailor a treatment regimen most suitable for the subject.

Experimental Results 1

In a first experiment, the correlation between exhaled breath and disease states was tested by measuring concentrations of a large number of volatile organic compounds (VOCs) in the exhaled breath of non-infected mice, and mice infected with *Borrelia hermsii*.

Figure 5:
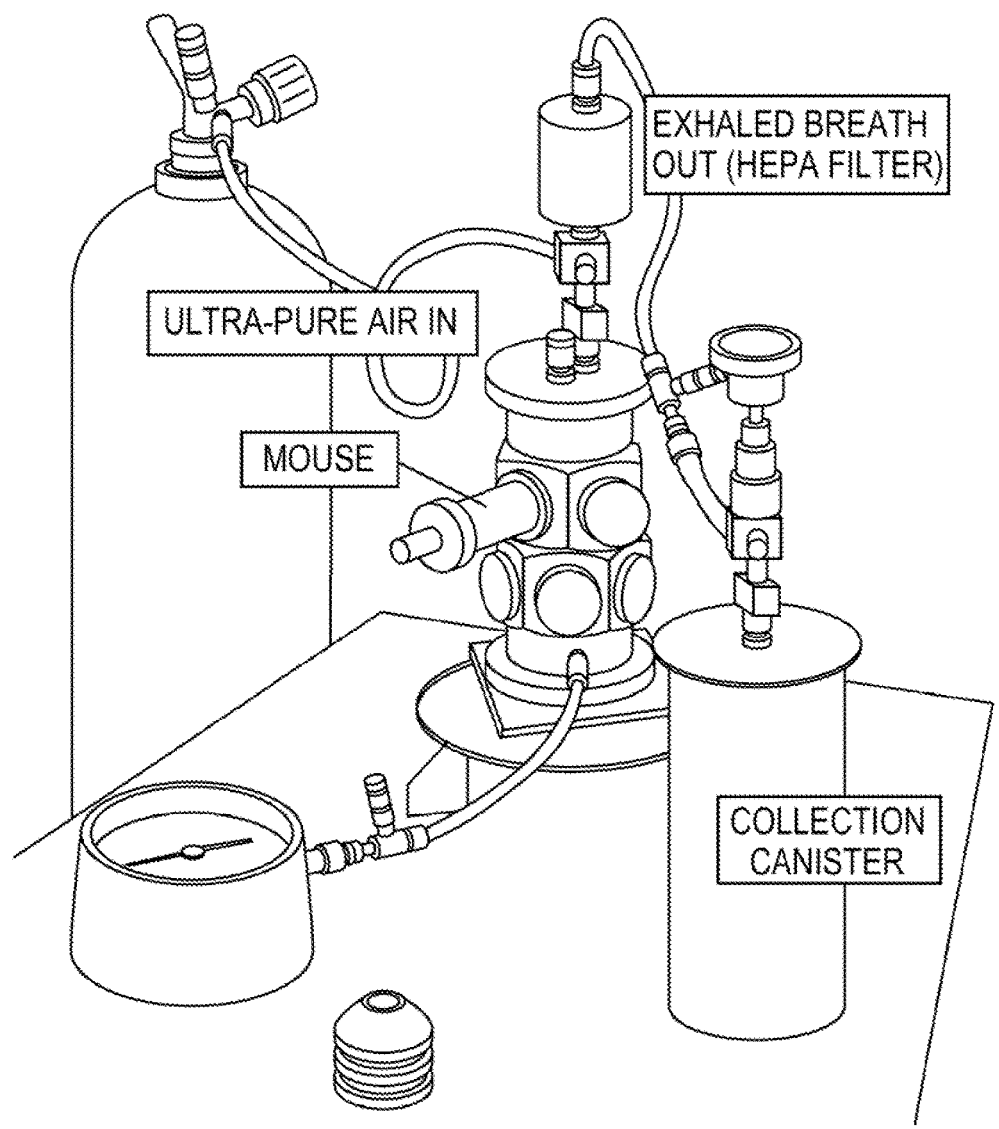
FIG. 5 illustrates a sample inhalation chamber used for breath analysis experiments conducted in mice according to an experimental study.

In the tested design, a cylindrical inhalation chamber with 12 ports for nose-only collection of breath samples was obtained from In-Tox products (Moriarty, N. Mex.), as shown in FIG. 5. The restraints were Lexan tubes (In-Tox) with an inner diameter of 3.1 cm and a length of 9.0 cm. The tubes were connected to the tower via O-ring-sealed, positive flow-by nose pieces with outlets of 28 mm diameter. The chamber was fitted with 0.25 inch ultratorr connectors (Swagelok) at inlet and outlet ports. Connected to the inlet of the chamber by stainless steel flex tubing was a pressurized cylinder of ultra-pure air, which was collected at 10,000 feet elevation at the University of California Crooked Creek White Mountain Research Center. A Whatman HEPA filter was attached at the outlet. Additionally, a pressure gauge was connected at the base of the chamber for continuous pressure monitoring throughout the procedure. Samples of the exhaled mouse breath were collected using 2 L electropolished stainless steel canisters under controlled dynamic flow conditions, via connection to the HEPA-filter at the outlet of the chamber.

The sample size of mice that were tested included 12 female and 12 male BALB/c scid mice aged 5-7 weeks old. They were first accommodated over seven days of training to restraint without distress for up to 10 minutes at nose-only ports of the inhalation chamber. Three mice at a time (one group), one at each port and grouped by sex, were positioned in the inhalation chamber for breath sampling. Ultra-pure air at a flow of 1 L/min was flushed through the tower for 6 minutes, and then while the air flow continued, a 2 min sample of exhaled breath for each mouse was collected. A blank sample of the ultra-pure air flushed through an empty port was also collected at the same session (sample of inhaled breath). Breath samples of all mice were collected on day −4, −2 and 0. All 24 mice were then infected with *Borrelia hermsii* on day 0 after the breath collection. Breath samples were again taken for all the mice on day 3 and day 5. The mice were sacrificed on day 6.

Seventy-three gases were detected and quantified in the breath of the mice. For the large majority of these gases, however, there was no discernible difference between the breath of infected and uninfected mice after correction for multiple testing. However, the only gaseous compound that was significantly elevated in the case of the infected mice when compared to the uninfected mice was carbon monoxide (CO).

Figure 6A:
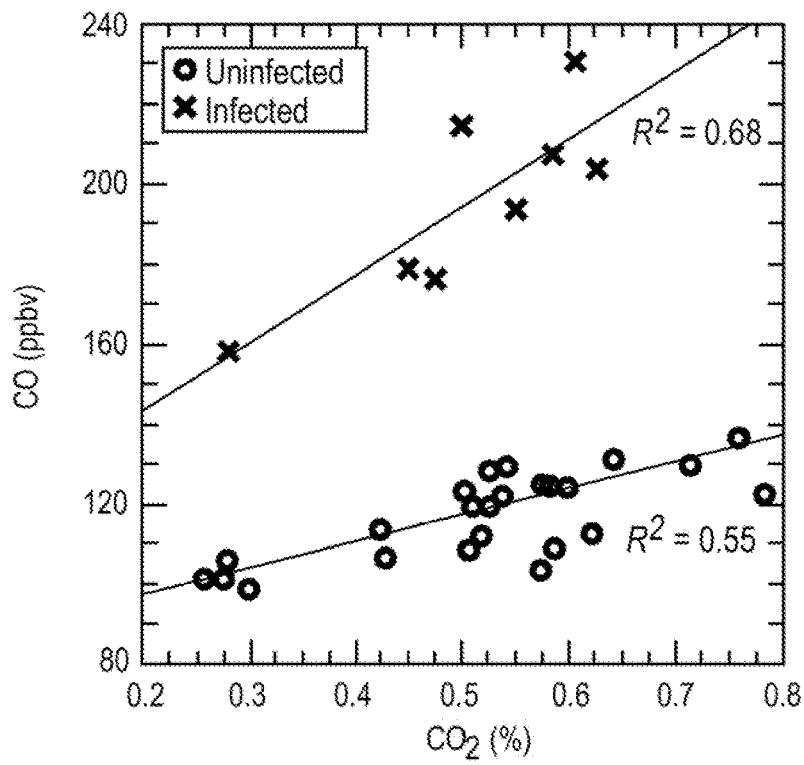
FIG. 6A illustrates CO and $CO_2$ concentrations for the mice of the first experimental study.

FIG. 6A shows differences in total CO concentrations in the canister samples between the 8 groups of mice on day 5 of infection and when they were uninfected on days −4, −2, and 0 were more apparent when these values were plotted against total $CO_2$ concentrations. CO concentration correlated with $CO_2$ under both uninfected and infected conditions but along different linear regressions. At a given $CO_2$ concentration, the CO in the sample from of a group of infected mice was about twice that from an uninfected group with a similar $CO_2$. It should be appreciated that this was confirmed in another experiment with 6-8 week-old male C.B-17-scid (n=24) that were infected with *B. hermsii* on day 0. Breath samples were collected on days 4 and 5 from these mice in 8 groups of 3 and from 18 uninfected mice in 6 groups of 3 (n=18).

Figure 6B:
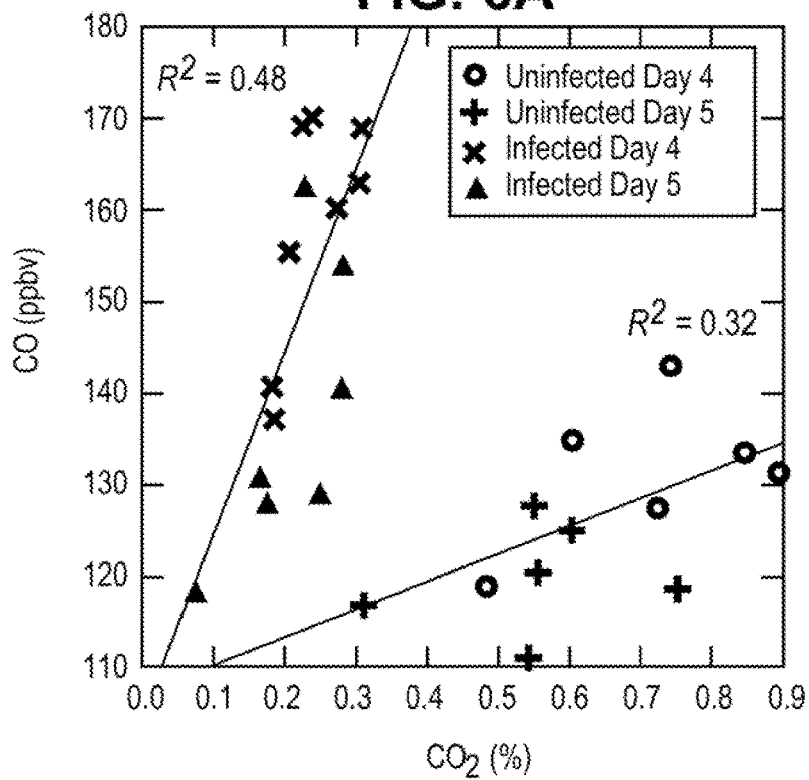
FIG. 6B illustrates another plot of CO and $CO_2$ for the mice of the first experimental study.

FIG. 6B shows a plot of total CO on $CO_2$ in the canister by infection state and day of sampling. While some of the uninfected mice groups had total CO concentrations in the collection canisters that were higher than collected samples from some infected groups, the $CO_2$ levels in samples from uninfected mice were up to 3-fold higher than corresponding infection samples. Based on these results, it was concluded that CO concentrations should be interpreted in the context of the measure of $CO_2$ in the sample.

The collected sample comprised both the exhaled breath and the residual ultra-pure air ("background") that was used to flush the system during the collection. For subsequent analyses the net amount attributable to mice in the samples was calculated by subtracting the background concentrations from the total concentrations of CO and $CO_2$. To take into account differences between mice in their ventilation during the sampling period, CO concentrations were normalized without units by dividing the net CO in ppbv by net $CO_2$ as %. This term is represented by the term "$CO/CO_2$".

Figure 7:
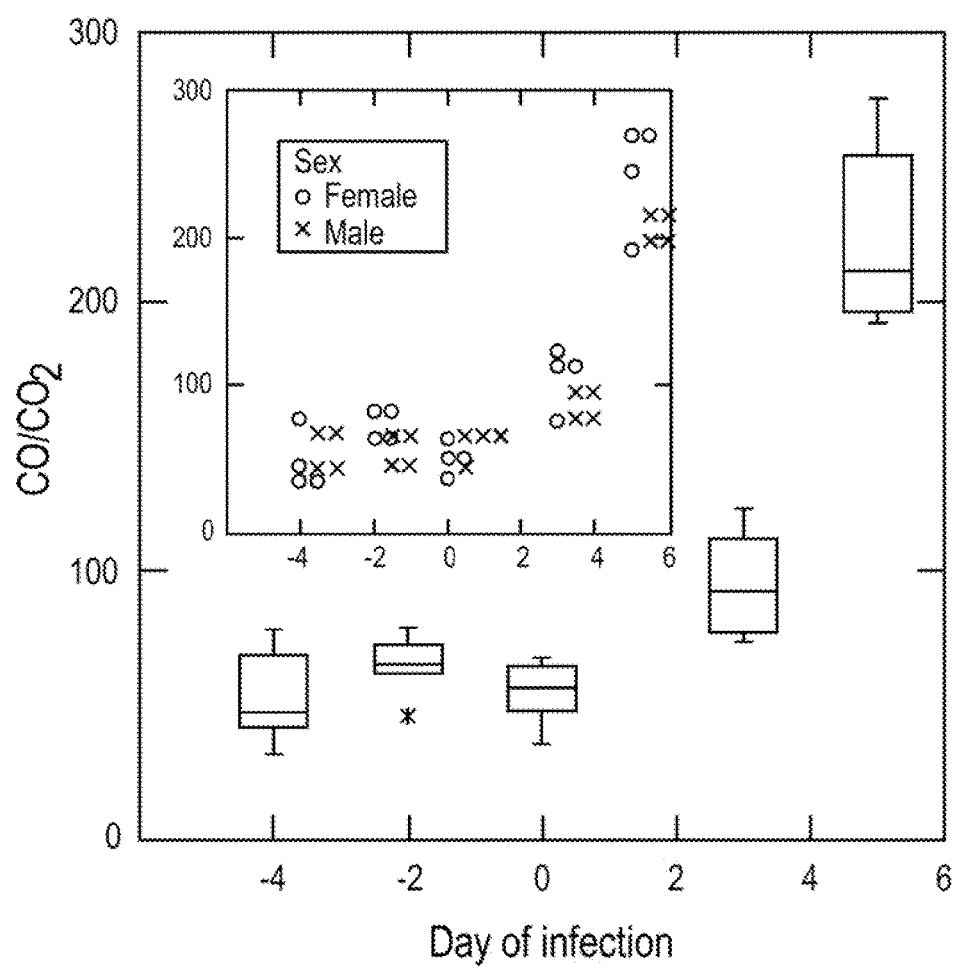
FIG. 7 illustrates $CO/CO_2$ concentrations from day −4 to day 6 in the first experimental study.

FIG. 7 shows the values of $CO/CO_2$ by day of the experiment for the 8 groups of BALB/c-scid mice before infection and then during infection by day. The $CO/CO_2$ values were stable on days −4, −2, and 0 before the injection and then markedly increased with progression of the infection over days 3 and 5. There was no apparent difference between groups of male and female mice in this response.

Experimental Results 2

Similar to above, another experiment was conducted to study the levels of $CO/CO_2$ for individual mice, using the same methods above. In this experiment, the daily blank values over 10 days of sampling averaged 0.036 (0.036-0.037) % for $CO_2$, and 89 (86-91) ppbv for CO. For 66 samples from 20 uninfected mice over 10 days, the mean total concentrations in the collected samples were 0.126 (0.114-0.138) % for $CO_2$, and 96 (95-97) for CO. The amount of $CO_2$ attributable to respiration by a mouse, i.e. after subtraction of the background value, gave net $CO_2$ values with unacceptably high variance for feasible sample sizes. As a modification, the flow of air was reduced from 1 L/min to 0.5 L/min and the collection period was increased from 2 to 4 min. The blank CO and $CO_2$ values over 12 days of collection were near-identical to the previous experiment, namely, 88 (86-90) ppbv and 0.036 (0.036-0.036) %. In contrast to the first experiment, however, for 100 samples from 18 uninfected mice over 12 days, the mean total concentrations in the canisters were 106 (105-107) for CO and 0.389 (0.373-0.405)% for $CO_2$, concentrations previously obtained only with groups of 3 or more mice.

By this modified protocol, exhaled breath of 18 male C.B-17-scid mice, aged 8-10 weeks was analyzed. The exhaled breath was measured on day −3 and day 0 (infection induced) and every day after the induced injection. Six mice received injection of BSK II medium alone. Five infected mice were treated with the antibiotic ceftriaxone on day 4 after breath samples were collected and daily for 4 days thereafter. Five of 7 untreated infected mice were euthanized after day 4's collection, and the other 2, as well as 2 uninfected mice, were euthanized after day 5. Four mice remained uninfected for the duration but received the same antibiotic treatment as for the infected animals.

Figure 8:
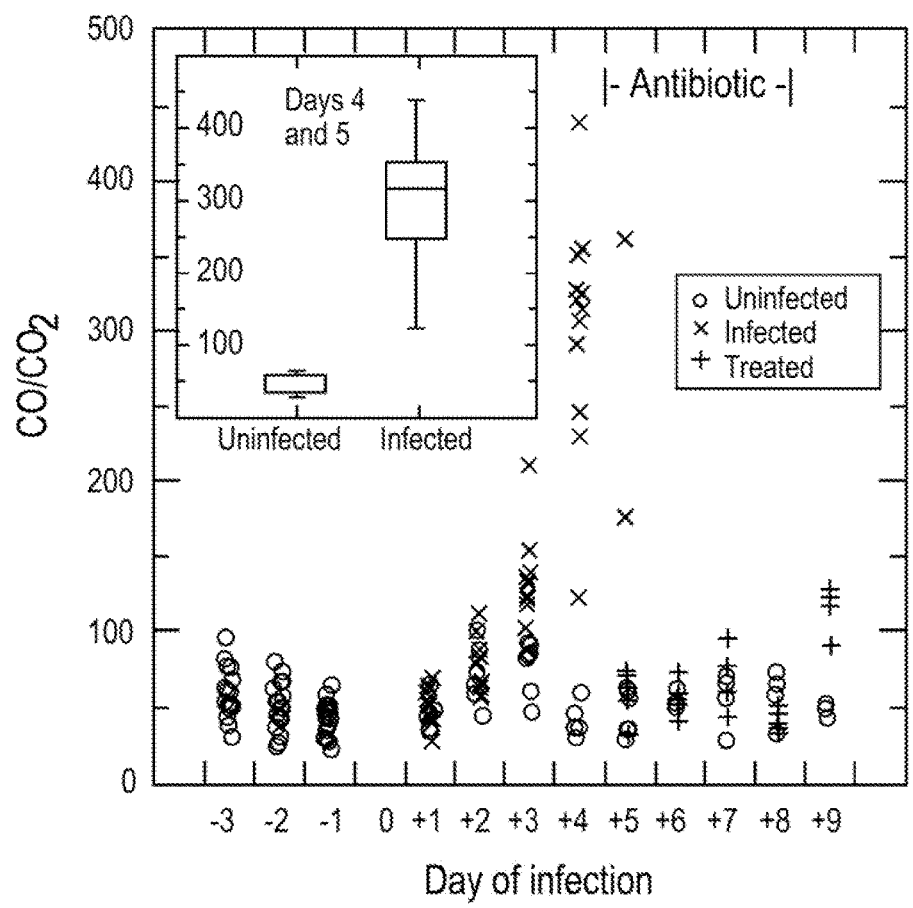
FIG. 8 illustrates $CO/CO_2$ concentrations over time for mice treated with different doses of antibiotics in a second experimental study.

FIG. 8 shows the values for $CO/CO_2$ for the mice by day and their status of uninfected, infected, or antibiotic-treated on the day of the study. While there was little difference between individual mice before infections were initiated or among uninfected mice throughout the experiment's course, $CO/CO_2$ rose over days 1 to 4 to values 4-fold higher than for uninfected animals. On days 4 and 5, when bacteria were near or at their peak in the blood, the effect size for infected over uninfected mice was 4.2 (2.8-5.6) with a r of 0.91 (p <0.0001). Remarkably, $CO/CO_2$ declined to the range of the uninfected mice within one day of the first dose of antibiotic. In contrast, infected mice who remained untreated continued to have elevated $CO/CO_2$ on that day.

Figure 9:
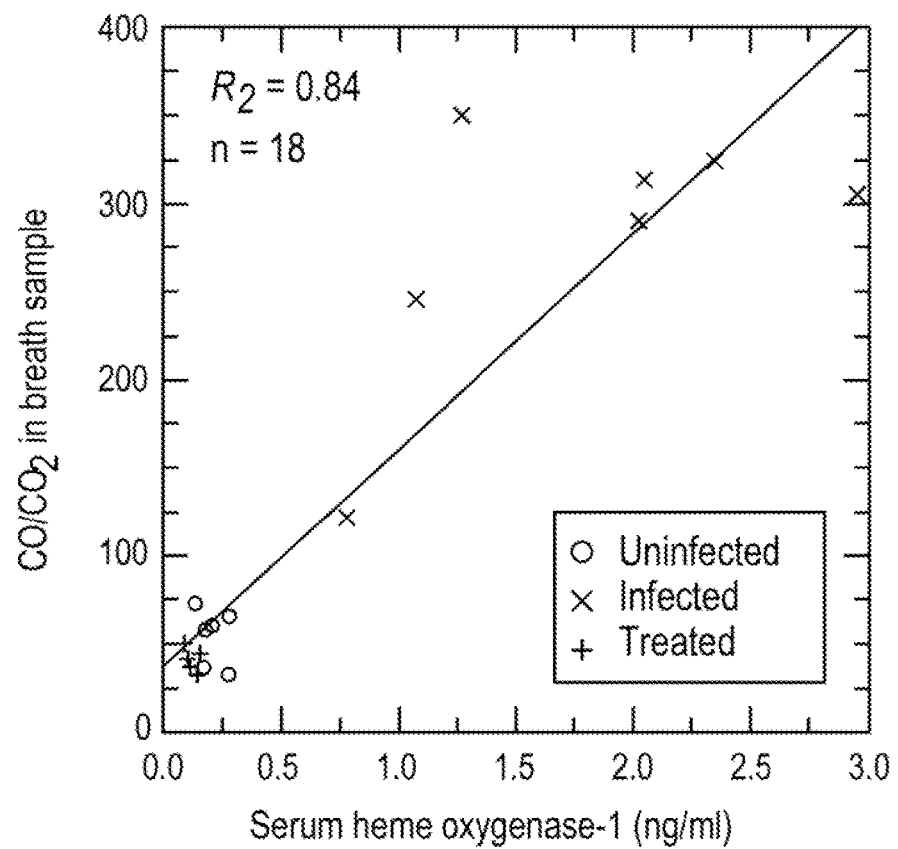
FIG. 9 illustrates heme oxygenase-1 levels and corresponding $CO/CO_2$ concentrations in the second experimental study.

The increase in CO in infected mice may be largely attributable to the action of the enzyme heme oxygenase-1 in tissues and the blood. To test this, the concentration of heme oxygenase-1 in the serum was measured, which was taken at the time of sacrifice from uninfected, infected, and treated BALB/c-scid mice (which were equally divided between males and females). Mean concentrations of the heme-oxygenase-1 (ng/ml) were 0.14 (0.01-0.28) for the 4 uninfected mice, 0.65 (0.43-0.87) for the 8 infected mice on day 4, and 0.05 (0.01-0.09) for the 8 antibiotic-treated mice after day 3. Among infected mice, females (0.58 [0.18-0.97]) and males (0.72 [0.48-0.96]) had similar values (p>0.5). As shown in FIG. 9 both $CO/CO_2$ and heme oxygenase levels were elevated in untreated infected mice in comparison to uninfected or treated mice. When the serum heme oxygenase concentration was >0.5 ng/ml (n=7), the $CO/CO_2$ value was >100; when the enzyme concentration was ≤0.5 ng/ml (n=12), the $CO/CO_2$ value was ≤100 (p<10-4).

It should be appreciated that in both the experiments above, CO was analyzed using a gas chromatograph (HP 5890) equipped with a flame ionization detector (FID) and a 3 m molecular sieve column (⅛" O.D.). The first 3.5 minutes of effluent from the column were vented to the laboratory. At 3.5 min a 4-way switching valve directed the column outflow to a nickel catalyst (2% coating on Chromosorb G) where the CO reacted with H2 to form methane ($CH_4$) that was detected by the FID set at 250° C. The oven temperature was kept at 60° C. for 2 min, then raised to 110° C. (at 70° C./min), and after 5 min returned to 60° C. for a new analysis. The carrier gas was helium, the CO retention time was 5.3 minutes, and the amount of sample injected was 10 mL. The system for $CO_2$ shared the manifold with the CO system. The sample was injected into a 6-foot long column (⅛" O.D.; Alltech) packed with 80/100 mesh Carbosphere. $CO_2$ was measured with the gas chromatograph equipped with a thermal conductivity detector set at 230° C. The oven temperature was kept at 150° C. for 2.5 min, then raised to 220° C. (at 70° C./min), and after 1.5 min returned to 150° C., for a new analysis. The carrier and reference gas used was helium; the $CO_2$ retention time was 1.5 minutes. For CO, accuracy and precision were 1% and 2 parts per billion by volume (ppbv), respectively; corresponding values for $CO_2$ were 1% and 3 parts per million by volume (ppmv). The analytical system for VOCs was a multi-column/detector combination gas-chromatographic system, and consisting of 6 different column detector combinations from among 2 FIDs, 2 electron capture detectors, and a mass spectrometer. The different column/detector combinations allowed for the identification and quantification of several different classes of VOCs, including hydrocarbons, halocarbons, sulfur compounds, oxygenated gases, and alkyl nitrates, with detection limit of 10 parts per trillion by volume (pptv) for all the gases.

It should further be appreciated that the *Mus musuclus* strains congenic with BALB/c with the severe combined immunodeficiency mutation (SCID) were CBySmn.C.B-17-Prkdcscid/J obtained from Jackson Laboratory (BALB/c-scid) and C.B-17/Icr-Prkdcscid/IcrlcoCrl from Charles River Laboratories (C.B-17-scid). BALB/cJ mice were from obtained Jackson Laboratory. Mice were housed in isolator cages under ABSL2 containment in an Association for Assessment and Accreditation of Laboratory Animal Care-approved facility, provided with autoclaved bedding and food (Harlan Teklad Global Soy Protein-Free Rodent Diet), were kept on a 12-h light-dark cycle, and received autoclaved distilled water ad libitum. Mice were examined and weighed daily. This study was carried out in strict accordance with the recommendations in the Guide for Care and Use of Laboratory Animals of the National Institutes of Health. The protocol was approved by the Institutional Animal Care and Utilization Committee of the University of California Irvine (protocol 2080-1999). Euthanasia and exsanguination was carried out under terminal anesthesia with isofluorane; all efforts were made to minimize suffering. *Borrelia hermsii* strain CC1 was passaged in mice or stored in plasma at −80° C. as described. Bacteria were cultivated in BSK II medium in tightly-capped polystyrene tubes. Bacteria counts in culture medium or blood were determined by phase microscopy with a Petroff-Hauser chamber or by quantitative PCR (pPCR) with primers and probe for a region of the single-copy 16S rDNA gene as described. DNA was extracted from 10 µl whole blood with DNeasy Blood Kit from Qiagen. With this volume of sample, the lower limit of quantitation of the qPCR assay was ~100 genomes per milliliter of whole blood. Mice were inoculated intraperitoneally with ~104 bacteria in plasma diluted in medium to a volume of 100 µl or medium alone. Infection was monitored by microscopy of tail vein blood. Infected mice were either euthanized 1 day after bacteremia reached its peak density or treated with the antibiotic ceftriaxone (Sigma) in doses of 25 µg/g administered twice-daily subcutaneously. During terminal anesthesia, blood was obtained with or without 1% sodium citrate, and the liver and spleen were removed and weighed. Plasma samples were subjected to bead-based immunoassays at Myriad RBM (Austin, Tex.) for the 59 analytes of the RodentMAP v. 2.0 panel (Table 1 below)

With regards to heme oxygenase-1, it should be appreciated that concentrations in ng/ml of mouse heme oxygenase 1 (HO-1) in serum diluted 1:8 were measured in duplicate at OD 450 nm on a Synergy 2 microtiter plate reader (Biotek) with a sandwich enzyme-linked immunosorbent assay (Mouse Heme Oxygenase-1 EIA, Takara Bio). A reverse-transcriptase qPCR for mouse heme oxygenase-1 gene (HMOX1) and beta actin transcripts were developed. Total RNA was isolated from freshly obtained citrated blood using Qiamp RNA Blood Mini Kit (Qiagen), and cDNA synthesis was performed with a Maxima First Strand cDNA kit (Thermo Scientific). qPCR was performed in duplicate with qPCR Master Mix Plus for SYBRGreen (Eurogentec) in a Rotorgene 6000 (Corbett) thermal cycler. The conditions were 10 min at 95° C. and then 40 cycles of 15 s at 95° C. and 1 min at 60° C. Standards were clones of the target in a plasmid vector. HMOX1 mRNA copies were normalized per 1000 copies of beta actin.

Experimental Results 3

Similar to the above two experiments, yet another experiment of breath analysis was conducted with *Mus Muculus*, aged 8-10 weeks, but this time injected with a single dose of *Escherichia coli* 0111:B4 lipopolysaccharide (LPS).

First, selected host responses to the doses of LPS for the experiment were examined. Individual mice were bled and euthanized at 4 or 24 hours after injection, and serum samples were analyzed by immunoassays for selected biomarkers of inflammation and innate immunity. BALB/c mice were injected intraperitoneally with 50 µg or 250 µg of *E. coli* LPS or water at hour 0. Two mice injected with water alone had interleukin-6 (IL-6) levels of 5.2 and ≤3.7 pg/ml after 24 hr; corresponding interleukin-10 (IL-10) levels were below the lower limit of quantitation for the assay. In contrast, at 4 hr after injection the IL-6 levels in pg/ml were 2,350 for 50 µg LPS and 10,400 for a 250 µg dose. Corresponding IL-10 levels in pg/ml were 2,040 and 4,440. At 24 hr the IL-6 level was 253 and IL-10 level was 1,030 in a mouse that received 250 µg LPS. Other elevated mouse serum proteins, cytokines, or chemokines after the LPS injections included CD40 ligand (CD154), tumor necrosis factor-α, macrophage inhibitory protein-1β (CCL4), monocyte chemotactic protein-1 (CCL2), and vascular endothelial growth factor-A, as shown in Table 1 above. In a separate experiment under the same conditions, the ratios of HMOX1 transcripts to 1000 actin mRNAs in whole blood were 3.4 in an untreated animal, 21.3 at 4 h after a 50 µg dose of LPS, and 25.7 at 4 h after a 250 µg dose, and 25.5 at 24 h after a 250 µg dose These results were evidence of a systemic inflammatory response to the LPS in this experimental model and that a time frame of ~3 days for measurements was suitable for a single dose. For the breath analysis experiment, male adult BALB/c mice, weighing between 22-27 g, were accommodated to the breath collection apparatus (same as above). Then, breath samples were non-invasively collected on each of 2 days at hours −47 and −23 as a baseline before the

TABLE 1

Selected serum biomarkers of BALB/c mice injected with lipopolysaccharide (LPS) or buffer at hour 0

| LPS dose (µg) | Time (h) | CD40-ligand (ng) [0.43][1] | Interleukin-6 (pg) [3.8] | Interleukin-10 (pg) [220] | Tumor necrosis factor-α (pg) [110] | Macrophage inhibitory protein-1β (pg) [53] | Monocyte chemotactic protein-1 (pg) [8] | Vascular endothelial growth factor-A (pg) [158] | Haptoglobin (µg) [121] |
|---|---|---|---|---|---|---|---|---|---|
| 0 | 24 | 3.5 | 5.2 | ≤219 | ≤109 | 104 | 245 | 644 | 128 |
| 0 | 24 | 1.7 | ≤3.7 | ≤219 | ≤109 | 104 | 210 | 438 | 132 |
| 50 | 4 | 8.7 | 2,350 | 2,040 | 330 | 48,800 | 6,900 | 3,720 | 136 |
| 250 | 4 | 10.4 | 10,400 | 4,440 | 360 | 59,000 | 6,100 | 3,400 | 134 |
| 250 | 24 | 21.5 | 253 | 1,030 | 160 | 999 | 5,480 | 1,850 | 170 |

[ ], reported lower limit of quantitation of each analysis and at the laboratory for that run.

injection of LPS at hour 0 in a single dose of 0 (n3), 50 (n3), or 250 µg (n4). That is, three mice received 0 µg of LPS, three mice received 50 µg of LPS and three mice received 250 µg of LPS. Breath samples were then collected at hours 4, 10, 25, 30, 49, 73, and 121.

C3H/HeJ mice received LPS at 10 µg/gm of body weight (5 HeJ and 6 HeOuJ mice) or water alone (3 HeOuJ mice). Breaths were collected before the injections and then at 4 h and 24 h post-injection, followed by euthanasia. The mean and variances of pre-injection body weights of the groups were not significantly different (Table 2 below).

TABLE 2

Characteristics of C3H strain mice treated with lipopolysaccharide (LPS) at hour 0

| Group (size) | C3H strain/ Treatment | Body weight (gm) at 0 h | Hematocrit (%) at 24 h | Spleen/body wt. (%) at 24 h | $\Delta CO/CO_2$ at 4 h | $\Delta CO/CO_2$ at 24 h |
|---|---|---|---|---|---|---|
| A (3) | HeOuJ/ Buffer | 26.4 (25.5-27.4) | 49 (47-50) | 0.34 (0.29-0.38) | −41 (−61--21) | +4 (−41-+45) |
| B (5) | HeJ/ LPS | 25.4 (24.1-26.7) | 48 (48-49) | 0.54 (0.51-0.57) | −24 (−53-+5) | −44 (−23--65) |
| C (6) | HeOuJ/ LPS | 25.8 (24.7-26.8) | 50 (49-52) | 0.36 (0.33-0.39) | +60 (+51-70) | +120 (+85-155) |
| Mean diff. B vs C | | 0.5 (−1.3-+2.3) | 1.9 (0.3-3.6) | −0.18 (−0.14--0.22) | 84 (52-116) | 164 (115-213) |
| p value[1] | | 0.57 | 0.03 | <0.0001 | <0.0001 | <0.0001 |

[1] t test

Figure 10:
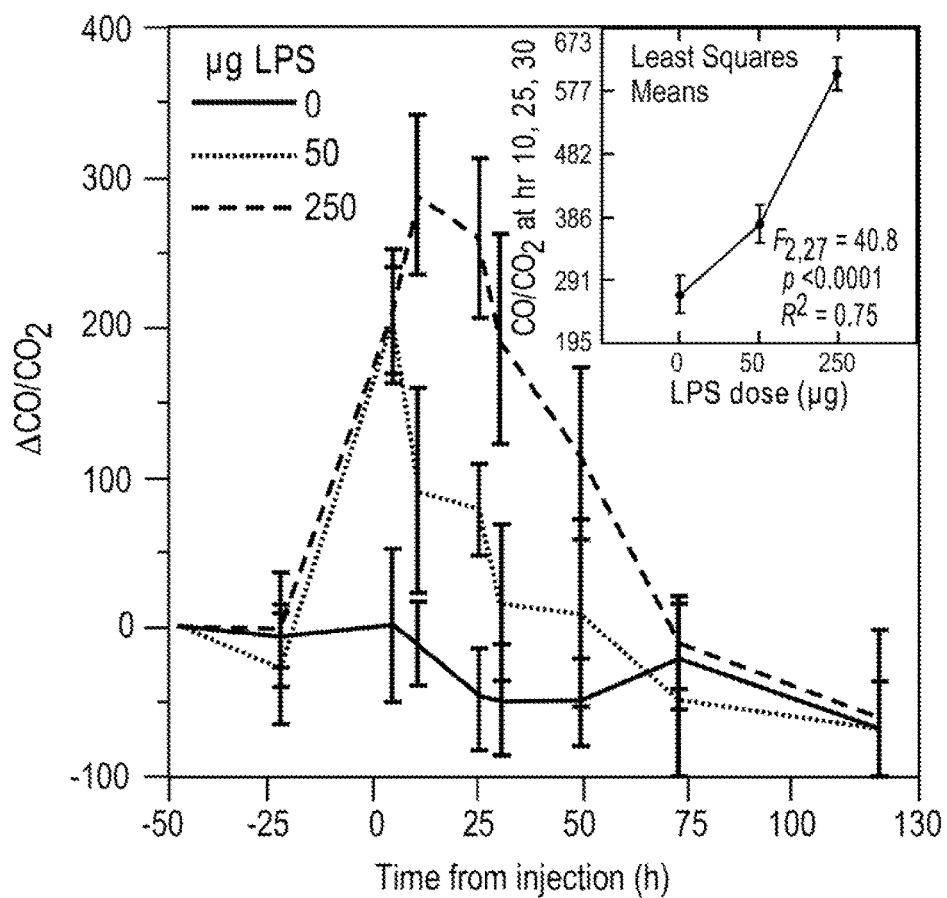
FIG. 10 illustrates $CO/CO_2$ concentrations over time for mice treated with different doses of LPS in the third experimental study.

Referring now to FIG. 10, the $CO/CO_2$ values increased over the first 24 hours after LPS injections and then declined over the next two days. Mice given the 250 µg dose had higher and later peak values than did mice with the 50 µg dose and a slower decline. The 250 µg dose mouse with the highest change in value from baseline, 816, died before the hour 49 collection. As the figure shows, there was trend toward lower $CO/CO_2$ values for the control mice over the course of the experiment. This may be attributable to further accommodation of the mice to the collection conditions and diminishing stress. For the collections at hours 10, 25, and 30, after control mouse values had already declined from baseline measures, there were significant dose-response differences between groups in absolute $CO/CO_2$ values.

This experiment confirmed the importance of normalizing CO for the $CO_2$ concentration in samples. With just CO concentrations in the collected samples, no differences between the treated mice and controls would have been noted. For the collections at 10, 25, and 30 h after injection of 250 µg LPS in 4 mice or water in 3 mice, the mean CO concentrations were 108 (105-112) for control mice and 110 (107-113) for treated mice (t and Kruskal Wallis tests p=0.4-0.5). But there was a marked difference between these groups in the % CO2 content, with mean values of 0.378 (0.339-0.416) for controls and 0.195(0.173-0.217) for treated mice (p<0.0001). This is accounted for the ~2-fold difference between groups in the CO/CO2 ratio: 292 (264-319) for controls and 583 (522-644) for treated mice (p<0.0001). Decreased physical activity and/or metabolism may have accounted for lower CO2 concentration in samples from LPS-treated mice. In one study injected endotoxin suppressed locomotor activity and food intake in mice.

The specificity of the CO response to endotoxin was also tested by studying C3H/HeJ (Tlr4Lps-d) mice, which, as the consequence of a spontaneous mutation in the toll-like receptor 4 gene, are more resistant to endotoxin. These were compared with mice, which are congenic but wild-type with respect to endotoxin sensitivity. The effect on HMOX1 expression in the blood of individual mice at 4, 18, and 42 post-injection of 0, 50, 100, or 250 µg LPS was first studied.

Figure 11:
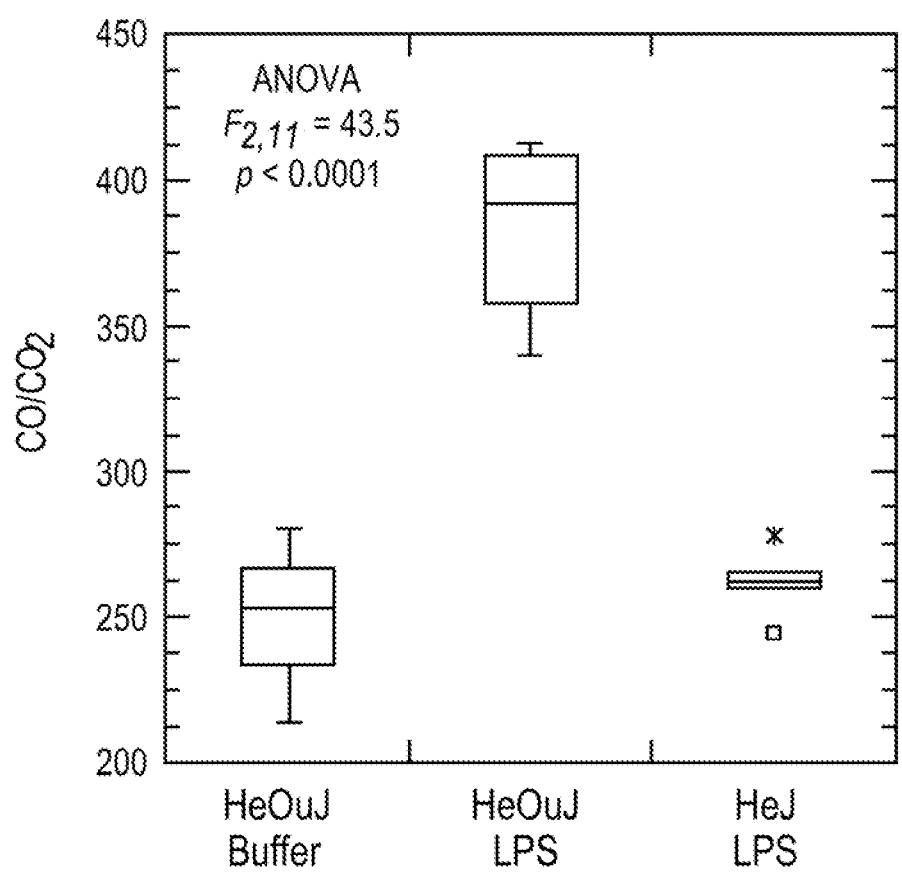
FIG. 11 illustrates $CO/CO_2$ concentrations for two different strains of mice in the third experimental study.
Figure 12:
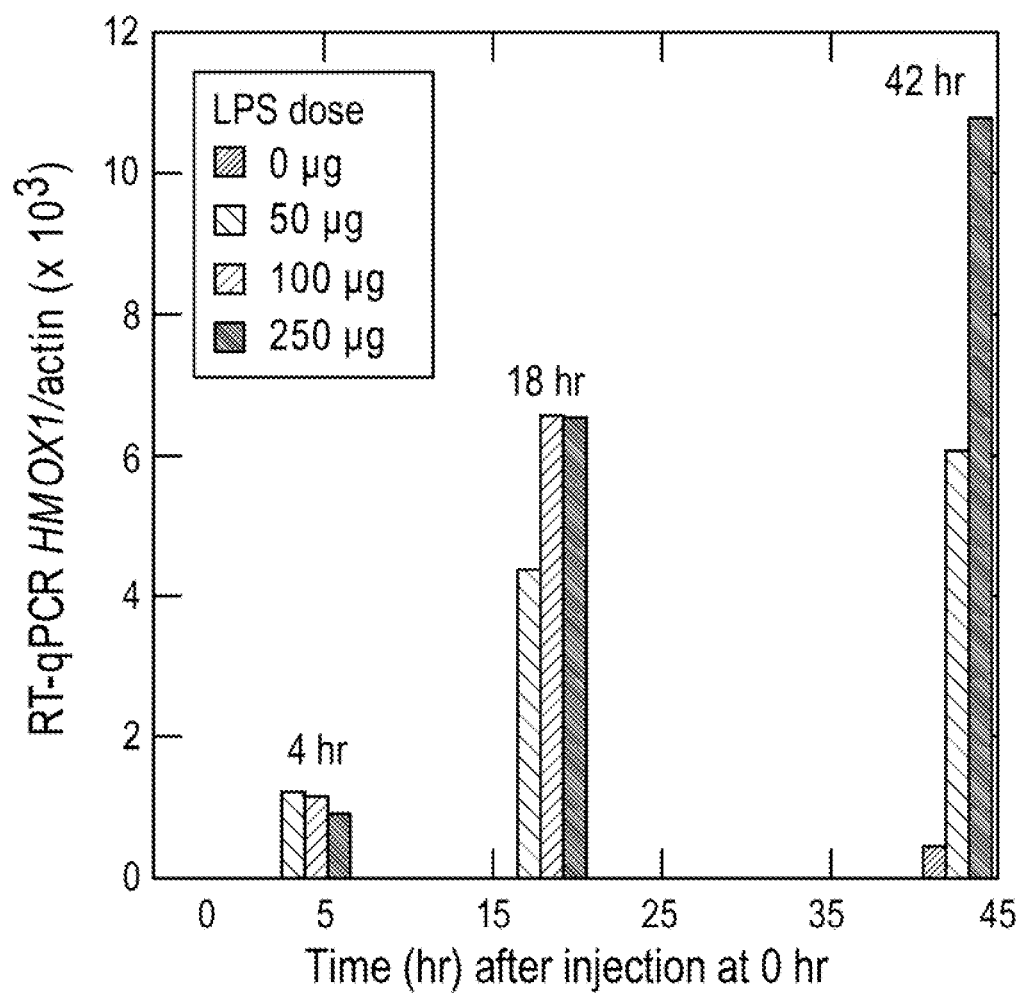
FIG. 12 illustrates HMOX1 levels over time for the mice treated with LPS in the third experimental study.

As shown in FIG. 11, the responses of the C3H lineage mice were similar to what was observed with BALB/c lineage mice. In the subsequent experiment C3H/HeOuJ or FIG. 12 shows the $CO/CO_2$ ratios for the hour 24 collection for the groups. The endotoxin-resistant mice were indistinguishable on this basis from the wildtype mice injected with buffer alone. These groups also significantly differed in $\Delta CO/CO_2$ from the hour 0 values at hours 4 and 24, as shown in Table 2. As expected, the wildtype mice injected with LPS had at the highest values for HMOX1 expression in the blood at hour 24 among the groups, but there was also moderate elevation for this parameter among the endotoxin-resistant mice as well. The mean HMOX1 copies were 7.1 (5.1-9.1) for HeOuJ mice treated with water, 21.4 (17.7-25.2) for HeJ mice treated with LPS, and 40.0 (28.8-51.1) for HeOuJ treated with LPS. These results indicated that the effect of LPS on CO production was at least partially mediated through toll-like receptor signaling and downstream pathways. They also confirmed the correlation between the heme oxygenase-1 activity in the blood and CO production, but also that transcription of HMOX1 may moderately increase in the blood without a concomitant increase in CO in certain backgrounds.

Another possible explanation for increased heme oxygenase-1 activity is hemolysis and resultant heme burden. However, there was no increase in haptoglobin after LPS treatment of the BALB/c mice (Table 1), and the treated HeOuJ mice did not have reduced hematocrits or larger spleens compared to treated HeJ mice (Table 2). Finally, histopathologic evaluation of hematoxylin and eosin-stained sections of the lungs showed no difference between HeOuJ mice who had received LPS (n=3) or water (n=3), an indication that increased exhaled CO was not attributable to pulmonary pathology.

The exhaled breath was not tested for nitric oxide (NO), another possible biomarker for inflammation. However, it should be appreciated that, in another study of mice treated with the same LPS and dose, NO in the exhaled breath rose ~30% by 10 hours after injection. In the present and previous studies, $CO/CO_2$ values were ~200% of the controls' values at a similar time interval.

It should be appreciated that the *Escherichia coli* 0111:B4 lipopolysaccharide (LPS), which had been phenol-extracted and chromatographically-purified by gel filtration and then passed through 0.2 µm pore-sized membrane as a 1.0 mg/ml aqueous solution, was from obtained from Sigma-Aldrich (catalog L5293). The LPS solution or water was further diluted for use in phosphate-buffered saline, pH 7.4 (PBS) solution in endotoxin-free Milli-Q (Millipore) water.

With regards to the mouse experiments, the protocol was approved by the Institutional Animal Care and Utilization Committee of the University of California Irvine. 8-10 week-old male BALB/cJ, C3H/HeJ (Tlr4Lps-d) and C3H/HeOuJ mice were obtained from The Jackson Laboratory (Bar Harbor, Me.). Mice were housed in isolator cages, kept on a 12-h light-dark cycle, and provided with autoclaved bedding, water, and food. Solutions in volumes of 250 µl were injected intraperitoneally. During terminal anesthesia, blood, spleens, and lungs were obtained. Spleens were weighed, and lungs fixed in 10% buffered formalin were processed for histopathology at University of California Davis' Comparative Pathology Laboratory. Plasma samples were subjected to bead-based immunoassays at Myriad RBM (Austin, Tex.) for the 59 analytes of the RodentMAP v. 2.0 panel. RT-qPCR for the mouse heme oxygenase-1 gene (HMOX1) and beta-actin transcripts was carried as described out on total RNA extracted from whole blood. Standards were clones of the targets in a plasmid vector. HMOX1 mRNA copies were normalized per 1000 copies of beta actin mRNA.

With regards to the collection and analysis of exhaled breath, it should be appreciated that breath samples from lightly-restrained, un-anesthetized mice, either individually or in groups of 5, were obtained with a nose-only multi-port collection chamber and attached HEPA filter and electropolished stainless steel canister as described above. The collected samples were effectively diluted ~10:1 from flushing with the ultra-pure air. The duration of the sampling for each mouse was between 3.8-4.0 min. Blanks for collection periods were taken from room air, which was filtered, constantly kept at 22° C. and in a smoking-free facility.

Similar to the previous two experiments, the processing of the breath samples for determination of CO and $CO_2$ by a Hewlett Packard 5890 gas chromatograph equipped with a flame ionization detector and thermal conductivity detector was carried out as described above. For CO, accuracy and precision were 1% and 2 parts per billion by volume, respectively; corresponding values for $CO_2$ were 1% and 3 parts per million by volume (ppmv). CO concentrations were normalized by dividing the total CO in ppbv by the integer value for the % CO2 content and representing this unit-less value by the term "CO/CO2". For means and differences, 95% confidence intervals are given in parentheses.

Experimental Results 4

In another experiment, exhaled breath of human subjects infected with malaria was analyzed along with a control group. The age of the human subjects ranged from 9 years old to 14 years old. There were 17 subjects total, out of which 8 had contracted malaria, while the remaining 9 were control subjects. Both inhaled and exhaled breath was collected for all the subjects, recording measurements of CO and $CO_2$ concentrations. The concentrations of CO and $CO_2$ in the inhaled breath were subtracted from the concentrations of CO and $CO_2$ in the exhaled breath of each of the subjects. The CO concentration was then normalized in the same manner described above.

Table 3 below shows a table of CO concentrations, CO2 concentrations, and the normalized CO concentrations (CO/CO2) for all seventeen subjects. The mean value for normalized CO concentration in the control subjects was 405, while the mean value for normalized CO concentration in subjects with malaria was 609. These results suggest that infection with the malaria parasite is associated with elevated levels of CO/CO2.

TABLE 3

| Subject | Age | CO | $CO_2$ | $CO/CO_2$ | Condition | Blood smear |
|---|---|---|---|---|---|---|
| 1 | 13 | 1495 | 4.76 | 272 | Malaria | 1 |
| 2 | 14 | 3695 | 4.06 | 862 | Malaria | 1 |
| 3 | 12 | 1783 | 1.89 | 837 | Malaria | 3 |
| 4 | 13 | 1807 | 4.86 | 331 | Malaria | 1 |
| 5 | 14 | 4703 | 4.42 | 1019 | Malaria | 1 |
| 6 | 11 | 2401 | 3.74 | 588 | Malaria | 3 |
| 7 | 9 | 1323 | 1.76 | 638 | Malaria | 2 |
| 8 | 13 | 3938 | 3.85 | 972 | Malaria | 1 |
| 9 | 11 | 2275 | 4.71 | 440 | Control | 0 |
| 10 | 9 | 1137 | 4.93 | 190 | Control | 0 |
| 11 | 12 | 1013 | 3.03 | 268 | Control | 0 |
| 12 | 13 | 1894 | 3.51 | 483 | Control | 0 |
| 13 | 14 | 1705 | 4.28 | 352 | Control | 0 |
| 14 | 14 | 2598 | 4.11 | 584 | Control | 0 |
| 15 | 13 | 2174 | 5.17 | 382 | Control | 0 |
| 16 | 13 | 2036 | 4.35 | 422 | Control | 0 |
| 17 | 14 | 2757 | 4.92 | 520 | Control | 0 |
| t test p value | | 0.014 | | Mean controls: | | 405 |
| Mann-Whitney p value | | 0.038 | | Mean Malaria: | | 690 |

While embodiments have been shown and described, various modifications may be made without departing from the scope of the inventive concepts disclosed herein. The invention(s), therefore, should not be limited, except to the following claims, and their equivalents.

What is claimed is:

1. A method comprising:
   collecting a sample of inhaled breath from a subject and measuring the concentration of carbon monoxide in the inhaled breath;
   collecting a sample of exhaled breath from the subject;
   measuring the concentration of carbon monoxide in the collected sample of inhaled breath;
   measuring the concentration of carbon monoxide in the collected sample of exhaled breath;
   determining a background-subtracted concentration of carbon monoxide by subtracting the measured concentration of carbon monoxide in the collected sample of inhaled breath from the measured concentration of carbon monoxide in the collected sample of exhaled breath;
   measuring the concentration of carbon dioxide in the collected exhaled sample;
   calculating a ratio of the concentration of the background-subtracted concentration of carbon monoxide to the concentration of carbon dioxide to determine a normalized concentration of carbon monoxide; and
   diagnosing a disease state based on the normalized concentration of carbon monoxide.

2. The method of claim 1, further comprising:
   comparing the normalized concentration of carbon monoxide to a predetermined set of values of concentration levels for the normalized concentration of carbon monoxide; and
   when the normalized concentration of carbon monoxide exceeds a particular predetermined value, diagnosing the subject with a disease state.

3. The method of claim 2, further comprising:
   administering a treatment regimen to the subject based on the disease state;

determining a follow-up normalized concentration of carbon monoxide in another collected sample of inhaled and exhaled breath from the subject, the other sample collected after the treatment regimen has commenced; and evaluating an effectiveness of the treatment regimen based on the determined follow-up normalized concentration of carbon monoxide.

4. The method of claim 1, wherein the disease state is an infection that is one of a parasite infection, a viral infection, a bacterial infection, or fungal infection.

5. The method of claim 4, wherein the infection comprises sepsis.

6. The method of claim 1, wherein the disease state comprises an autoimmune disease.

7. A method comprising:
collecting a set of samples of inhaled breath and exhaled breath from a subject over a period of time;
measuring the concentration of carbon monoxide in the samples of inhaled breath and exhaled breath;
determining a background-subtracted concentration of carbon monoxide in the set of samples by subtracting the measured concentration of carbon monoxide in the collected samples of inhaled breath from the measured concentration of carbon monoxide in the collected samples of exhaled breath;
normalizing the background-subtracted concentrations of carbon monoxide to a measured concentration of carbon dioxide to generate normalized concentrations of carbon monoxide;
determining a change in the normalized concentration of carbon monoxide over the period of time; and
evaluating an inflammatory state of the subject based on the determined change in the normalized concentration of carbon monoxide.

8. The method of claim 7, wherein the inflammatory state comprises an infection comprising one of a viral infection, a parasite infection, a bacterial infection, and a fungal infection.

9. The method of claim 7, wherein the inflammatory state comprises an autoimmune disease.

10. The method of claim 7, wherein the inflammatory state comprises trauma.

11. A device, comprising:
a breath collector configured to receive inhaled and exhaled breath from a subject;
one or more sensors configured to output a concentration of carbon monoxide in the received inhaled and exhaled breaths and to output a concentration of carbon dioxide in the received exhaled breath; and
a processor operably coupled to the one or more sensors and further configured to calculate a background-subtracted concentration of carbon monoxide by subtracting the measured concentration of carbon monoxide in the received inhaled breath from the measured concentration of carbon monoxide in the received exhaled breath and further calculate a ratio of the background-subtracted concentration of carbon monoxide to the concentration of carbon dioxide.

12. The device of claim 11, wherein the processor is further configured to output a diagnosis of a disease state based on the ratio.

13. The device of claim 12, wherein the disease state is one of a viral infection, bacterial infection, parasite infection, and fungal infection.

14. The device of claim 11, wherein the processor is further configured to compare the ratio to a set of predetermined values representative of the presence or absence of a disease state, wherein the presence or absence of the disease state is output when the ratio exceeds a corresponding predetermined value.

15. The device of claim 11, wherein the sensor outputs real-time or near real-time concentrations of carbon monoxide and carbon dioxide.

* * * * *